| United States Patent [19] | [11] Patent Number: 4,957,921 |
| --- | --- |
| Caprathe et al. | [45] Date of Patent: Sep. 18, 1990 |

[54] SUBSTITUTED CYCLOHEXANOLS AS CENTRAL NERVOUS SYSTEM AGENTS

[75] Inventors: Bradley W. Caprathe, Redford; Juan C. Jaen, Plymouth; Sarah J. Smith; Lawrence D. Wise, both of Ann Arbor, all of Mich.

[73] Assignee: Warner-Lambert Company, Morris Plains, N.J.

[21] Appl. No.: 446,901

[22] Filed: Dec. 6, 1989

[51] Int. Cl.$^5$ ............... A61K 31/495; A61K 31/44; A61K 31/445; A61K 31/505; C07D 401/14; C07D 409/14
[52] U.S. Cl. .................... 514/252; 514/210; 514/212; 514/227.5; 514/227.8; 514/235.5; 514/235.8; 514/256; 514/316; 514/317; 514/318; 514/326; 514/340; 514/343; 540/596; 540/597; 540/598; 540/601; 544/60; 544/63; 544/121; 544/122; 544/123; 544/124; 544/129; 544/193; 544/209; 544/212; 544/214; 544/216; 544/268; 544/275; 544/280; 544/295; 544/296; 544/357; 544/360; 544/364; 544/369; 544/379; 546/208; 546/209; 546/216; 546/275; 546/281; 546/344; 548/950; 548/962
[58] Field of Search .................... 544/60, 63, 121–124, 544/129, 193, 209, 212, 214, 216, 268, 275, 280, 295, 296, 357, 360, 364, 369, 379; 540/596–598, 601; 548/950, 962; 546/216, 186, 187, 188, 194, 208, 209, 275, 281, 344; 514/210, 212, 227.5, 227.8, 235.5, 235.8, 252, 256, 316, 317, 318, 326, 340, 343

[56] References Cited

U.S. PATENT DOCUMENTS

| 4,329,353 | 5/1982 | Stokbroekx et al. | 546/199 |
| 4,762,843 | 8/1988 | Caprathe et al. | 514/293 |

FOREIGN PATENT DOCUMENTS 790836 4/1973 Belgium .

OTHER PUBLICATIONS

Tamminga et al., Arch Gen Psychiatry, vol. 43, pp. 398–402 (1986).

*Primary Examiner*—Cecilia Shen
*Attorney, Agent, or Firm*—Francis J. Tinney

[57] ABSTRACT

Substituted cyclohexanols are described, as well as methods for the preparation and pharmaceutical composition of same, which are useful as central nervous system agents and are particularly useful as dopaminergic, antipsychotic, and antihypertensive agents as well as for treating hyperprolactinaemia-related conditions and central nervous system disorders.

6 Claims, No Drawings

SUBSTITUTED CYCLOHEXANOLS AS CENTRAL NERVOUS SYSTEM AGENTS

BACKGROUND OF THE INVENTION

The present invention relates to novel substituted cyclohexanols useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are dopaminergic agents.

A series of 1-(4-arylcyclohexyl)piperidines which may structurally be represented by the formula

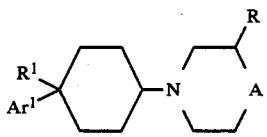   I the pharmaceutically acceptable acid addition salts and the stereochemically isomeric forms thereof, wherein $Ar^1$ is a member selected from the group consisting of aryl and 1,3-benzodioxolyl;

R is a member selected from the group consisting of hydrogen and lower alkyl;

$R^1$ is a member selected from the group consisting of hydrogen, cyano, carboxyl, lower alkyloxycarbonyl, aryllower alkyloxycarbonyl, aminocarbonyl, mono- and di(lower alkyl)aminocarbonyl, mono- and di(aryllower alkyl)aminocarbonyl, (aryllower alkyl)lower alkylamino carbonyl, hydroxy, lower alkyloxy, lower alkylcarbonyloxy, formyl, lower alkylcarbonyl, arylcarbonyl, aryllower alkylcarbonyl, lower alkyl, lower alkenyl, lower alkynyl and cyclohexyl; and A is a bivalent radical, having the formula

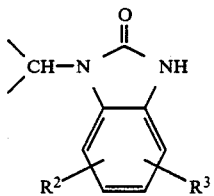   (a)

wherein $R^2$ and $R^3$ are each independently selected from the group consisting of hydrogen, halo, trifluoromethyl, lower alkyl, and lower alkyloxy; or A is a bivalent radical, having the formula

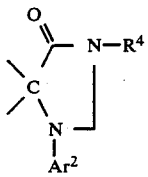   (b)

wherein $Ar^2$ is aryl, and $R^4$ is a member selected from the group consisting of hydrogen, lower alkyl, aryllower alkyl, cyanolower alkyl, aminolower alkyl, mono- and di(lower alkyl) aminolower alkyl, mono- and di(aryllower alkyl)aminolower alkyl, [(aryllower alkyl)lower alkylamino]lower alkyl, hydroxylower alkyl, mercaptolower alkyl, lower alkyloxylower alkyl, lower alkylthiolower alkyl, aryloxylower alkyl, arylthiolower alkyl, aryllower alkyloxylower alkyl, aryllower alkylthiolower alkyl, and a radical of formula

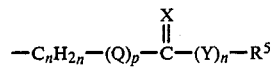

wherein n is 0 or an integer of from 1 to 6 inclusive, Q is O, S or $NR^6$, p is 0 or 1, X is O or S, $R^5$ is hydrogen, lower alkyl, aryl or aryllower alkyl, m is 0 or 1 and Y is O, S or $NR^6$, wherein $R^6$ as used in the definition of Q and Y is hydrogen, lower alkyl, aryl or aryllower alkyl;

provided that when Y is O and m and p are each 1, then $R^5$ is other than hydrogen and provided that when p is 1 then n is other than 0:

wherein aryl is a member selected from the group consisting of phenyl, thienyl, pyridinyl, naphthalenyl and substituted phenyl, said substituted phenyl having from 1 to 3 substituents each independently selected from the group consisting of halo, lower alkyl, lower alkyloxy, phenyl lower alkyloxy, trifluoromethyl, nitro, amino and hydroxy are disclosed in U.S. Pat. No. 4,329,353 as having psychotropic and antiemetic activity.

A series of 4-alkoxy-4-(substituted phenyl)cyclohexylamines of formula

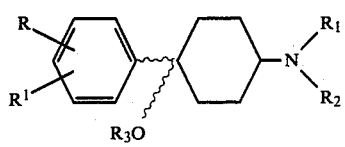

where the ⌇ sign indicates the cis or trans configuration the condition that when the $R_3O$ bond is cis with respect to the amino group the bond joining the phenyl and cyclohexyl rings is trans and vice versa; R=1-4C alkyl, Cl, F, Br, $CF_3$, or 1-4C alkoxy; R'=R or H; $R_1$=H or 1-4C alkyl; $R_2$=H, 1-4C alkyl, aroylalkyl (monosubstituted on the aryl ring by a group R or 6-10C aryl) or bis-arylalkyl (monosubstituted on the ring by a group R' or 6-10C aryl) or $R_1$ and $R_2$ together with the N atom form a saturated heterocyclic chosen from pyrrolidino, piperidino, hexamethyleneimino, morpholino, and piperazino (optionally monosubstituted); $R_3$=1-4C alkyl; are disclosed in Belgium Patent No. 790836 as having central nervous system depressant activity.

However, the 1-(4-arylcyclohexyl)piperidines disclosed in U.S. Pat. No. 4,329,353 and the 4-alkoxy-4-(substituted phenyl)-cyclohexylamines disclosed in Belgium Patent 790836 do not disclose or suggest the combination of structural variations of the compounds of the present invention described hereinafter.

SUMMARY OF THE INVENTION

Accordingly, the present invention is a compound of Formula I

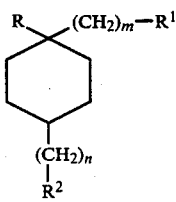

wherein

R is —OR³, wherein R³ is hydrogen, lower alkyl, aryl lower alkyl, lower alkanoyl, aroyl, or aryl lower alkanoyl,

wherein R⁴ and R⁵ are each independently hydrogen, lower alkyl, aryl, aryl lower alkyl, lower alkanoyl, aryl lower alkanoyl, aroyl, or R⁴ and R⁵ are taken together with the nitrogen atom to which they are attached to form a ring denoted by

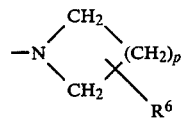

wherein p is zero or an integer from 1 to 4 and R⁶ is hydrogen or lower alkyl,

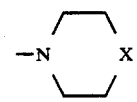

wherein X is oxygen or sulfur or

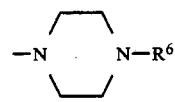

wherein R⁶ is as defined above, or

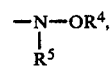

wherein R⁴ and R⁵ are each independently hydrogen, lower alkyl, aryl, aryl lower alkyl, lower alkanoyl, aryl lower alkanoyl, aroyl, or R⁴ and R⁵ are taken together with the oxygen and nitrogen atoms to which they are attached to form a ring denoted by

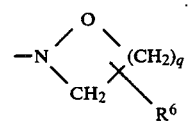

wherein q is an integer from 2 to 3 and R⁶ is as defined above;

m is zero or an integer from 1 to 2;

R¹ is aryl, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen;

n is zero or an integer from 1 to 4;

R² is

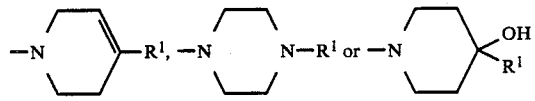

wherein R¹ is as defined above; and the corresponding cis and trans isomers thereof; or a pharmaceutically acceptable acid addition salt thereof.

As dopaminergic agents, the compounds of Formula 1 are useful as antipsychotic agents for treating psychoses such as schizophrenia. They are also useful as antihypertensives and for the treatment of disorders which respond to dopaminergic activation. Thus, other embodiments of the present invention include the treatment, by a compound of Formula I, of hyperprolactinaemia-related conditions, such as galactorrhea, amenorrhea, menstrual disorders and sexual dysfunction, and several central nervous system disorders such as Parkinson's disease, Huntington's chorea, and depression. In addition, like many known antipsychotics, these compounds are high affinity ligands for the central nervous system sigma binding site.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

The term "aryl" means an aromatic radical which is a phenyl group or phenyl group substituted by one to four substituents selected from lower alkyl, lower alkoxy, lower thioalkoxy, halogen or trifluoroethyl such as, for example, benzyl, phenethyl, and the like.

The term "aryl lower alkyl" means an aromatic radical, as defined above, attached to a lower alkyl group as defined above.

The term "lower alkanoyl" means a lower alkyl group as defined above attached to a carbonyl group which is then attached to the parent molecular residue.

The term "aryl lower alkanoyl" means an aromatic radical, as defined above, attached to a lower alkanoyl group as defined above.

The term "aroyl" means an aromatic radical as defined above attached to a carbonyl group which is then attached to the parent molecular residue.

"Lower alkoxy" and "thioalkoxy" are O-alkyl or S-alkyl of from one to six carbon atoms as defined above for "lower alkyl."

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium and the like.

Pharmaceutically acceptable acid addition salts of the compounds of Formula 1 include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesufonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science*, Vol. 66, pages 1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the present invention may exist as a mixture of cis and trans isomers or as the individual cis and trans isomers. The mixture of isomers as well as the individual isomers are intended to be encompassed within the scope of the present invention.

A preferred compound of Formula I is one wherein R is —OR³, wherein R³ is hydrogen or lower alkanoyl,

wherein R⁴ is hydrogen or lower alkanoyl and R⁵ is hydrogen or

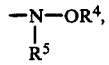

wherein one of $R^4$ or $R^5$ is hydrogen and the other is hydrogen, lower alkyl, aryl, or lower alkanoyl;

m is zero;

$R^1$ is phenyl, phenyl substituted by para lower alkyl, para lower alkoxy, para lower thioalkoxy, or para halogen, 2-, 3-, or 4-pyridinyl, 2-, or 3-furanyl, 2- or 3-thienyl, 2-, 4-, or 5-thiazolyl, or 2-, 4-, or 5-pyrimidinyl;

n is zero or an integer from 1 to 3; and $R^2$ is

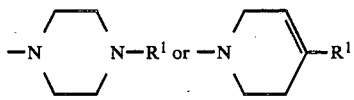

wherein $R^1$ is as defined above.

Another preferred embodiment is a compound of Formula I wherein

R is —OH, —NH₂, or

—NHOR⁴, wherein $R^4$ is hydrogen, lower alkyl, aryl, or lower alkanoyl;

m is zero;

$R^1$ is phenyl, phenyl substituted by para lower alkoxy or para halogen, 2-, 3-, or 4-pyridinyl, 2- or 3-thienyl, 2-, 4-, or 5-thiazolyl, or 2-, 4-, or 5-pyrimidinyl;

n is zero or an integer from 1 to 2; and $R^2$ is

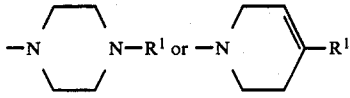

wherein $R^1$ is as defined above.

Particularly valuable are:
4-[2-[4-(2Pyridinyl)-1-piperazinyl]ethyl]-1-(2-thienyl)-cyclohexanol (mixture of cis/trans);
cis-4-[2-[4-(2-Pyridinyl)-1-piperazinyl]ethyl]-1-(2-thienyl)cyclohexanol;
trans-4-[2-[4-(2-Pyridinyl)-1-piperazinyl]ethyl]-1-(2-thienyl)cyclohexanol;
1-Phenyl-4-[2-[4-(2-pyridinyl)-1-piperazinyl]ethyl]cyclohexanol (mixture of cis/trans);
1-(2-Pyridinyl)-4-[2-[4-(2-pyridinyl)-1-piperazinyl]ethyl]cyclohexanol (mixture of cis/trans);
1-(4-Fluorophenyl)-4-[2-[4-(2-pyridinyl)-1-piperazinyl]ethyl]cyclohexanol (mixture of cis/trans);
cis-1-(4-Methoxyphenyl)-4-[2-[4-(2-pyridinyl)-1-piperazinyl]ethyl]cyclohexanol;
trans-1-(4-Methoxyphenyl)-4-[2-[4-(2-pyridinyl)-1-piperazinyl]ethyl]cyclohexanol;
4-[2-4-(2-Pyridinyl)-1-piperazinyl]ethyl]-1-(2-thiazolyl)-cyclohexanol (mixture of cis/trans);
1-(3-Pyridinyl)-4-[2-[4-(2-pyridinyl)-1-piperazinyl]ethyl]cyclohexanol (mixture of cis/trans);
cis-1-(2-Pyridinyl)-4-[2-[3,6-dihydro-4-phenyl-1(2H)-pyridinyl]ethyl]cyclohexanol;
cis-1-(3-Pyridinyl)-4-[2-[3,6-dihydro-4-phenyl-1(2H)-pyridinyl]ethyl]cyclohexanol;
cis-4-[2-(3,6-Dihydro-4-phenyl-1(2H)-pyridinyl)ethyl]-1-(2-thienyl)cyclohexanol;

4-[2-[4-(2-Pyridinyl)-1-piperazinyl]ethyl]-1-(3-thienyl)-cyclohexanol (mixture of cis/trans);
trans-4-[[4-(2-Pyridinyl)-1-piperazinyl]methyl]-1-(2-thienyl)cyclohexanol;
cis-4-[[4-(2-Pyridinyl)-1-piperazinyl]methyl]-1-(2-thienyl)cyclohexanol;
trans-1-(2-Pyridinyl)-4-[4-(2-pyrimidinyl)-1-piperazinyl]cyclohexanol;
cis-1-(2-Pyridinyl)-4-[4-(2-pyrimidinyl)-1-piperazinyl]cyclohexanol;
trans-1-(2-Pyridinyl)-4-[4-(2-pyridinyl)-1-piperazinyl]cyclohexanol;
cis-1-(2-Pyridinyl)-4-[4-(2-pyridinyl)-1-piperazinyl]cyclohexanol;
trans-1-(3-Pyridinyl)-4-[4-(2-pyridinyl)-1-piperazinyl]cyclohexanol;
cis-1-(3-Pyridinyl)-4-[4-(2-pyridinyl)-1-piperazinyl]cyclohexanol;
4-[4-(2-Pyridinyl)-1-piperazinyl]-1-(2-thienyl)cyclohexanol (mixture of cis/trans);
4-[4-(2-Pyridinyl)-1-piperazinyl]-1-(3-thienyl)cyclohexanol (mixture of cis/trans);
trans-1-(4-Chlorophenyl)-4-[4-(2-pyridinyl)-1-piperazinyl]cyclohexanol;
cis-1-(4-Chlorophenyl)-4-[4-(2-pyridinyl)-1-piperazinyl]cyclohexanol
1-Methoxyphenyl-4-[4-(2-pyridinyl)-1-piperazinyl]cyclohexanol (mixture of cis/trans);
1-Phenyl-4-[4-(2-pyridinyl)-1-piperazinyl]cyclohexanol (mixture of cis/trans);
4-(3,6-Dihydro-4-phenyl-1(2H)-pyridinyl)-1-(2-pyridinyl)cyclohexanol (mixture of cis/trans);
trans-4-(3,6-Dihydro-4-phenyl-1(2H)-pyridinyl)-1-(3-pyridinyl)cyclohexanol; and
cis-4-[3,6-Dihydro-4-phenyl-1(2H)-pyridinyl]-1-(3-pyridinyl)cyclohexanol;
or a pharmaceutically acceptable acid addition salt thereof.

The compounds of Formula I are valuable dopaminergic agents. The tests employed indicate that compounds of Formula I possess dopaminergic activity. Thus, the compounds of Formula I were tested for their ability to inhibit locomotor activity in mice according to the assay described by J. R. McLean, et al, *Pharmacology, Biochemistry and Behavior*, Volume 8, pages 97–99 (1978); for their ability to inhibit [$^3$H]-spiroperidol binding in a receptor assay described by D. Grigoriadis and P. Seeman, *Journal of Neurochemistry*, Volume 44, pages 1925–1935 (1985); and for their ability to inhibit dopamine synthesis in rats according to the protocol described by J. R. Walters and R. H. Roth, *Naunyn-Schmiedeberg's Archives of Pharmacology*, Volume 296, pages 5–14 (1976). The above test methods are incorporated herein by reference. The data in the table show the dopaminergic activity of representative compounds of Formula I. Additionally, the compounds of Formula I are ligands for the sigma opiate binding site. The data in the table show the inhibition of [$^3$H]DTG (ditoluoyl guanidine; a sigma ligand) binding by representative compounds of Formula I, according to the method of E. Weber, et al, *Proceedings of the National Academy of Sciences, USA*, Volume 83, pages 8784–8788 (1986).

| | Biological Activity of Compounds of Formula I | | | | |
|---|---|---|---|---|---|
| Example Number | Compound | Inhibiton of [$^3$H]-Spiroperidol Binding IC$_{50}$ nM | Inhibition of Locomotor Activity in Mice ED$_{50}$, mg/kg, IP | Effects on Brain Striatal Dopamine Synthesis in Rats at 10 mg/kg, IP | Inhibition of [$^3$H]DT Binding IC$_{50}$ nM |
| 1 | trans-1-(4-Chlorophenyl)-4-[4-(2-pyridinyl)-1-piperazinyl]cyclohexanol | 333 | 2.3 | | |
| 1a | cis-1-(4-Chlorophenyl)-4-[4-(2-pyridinyl)-1-piperazinyl]cyclohexanol | 816 | 0.86 | | |
| 3 | cis-4-[2-[4-(2-Pyridinyl)-1-piperazinyl]-ethyl]-1-(2-thienyl)cyclohexanol | 262 | 1.3 | 67% inhibition | 6.0 |
| 4 | trans-4-[2-[4-(2-Pyridinyl)-1-piperazinyl]-ethyl]-1-(2-thienyl)cyclohexanol | 341 | 1.1 | 47% inhibition | 5.0 |
| 5 | 1-Phenyl-4-[2-[4-(2-pyridinyl)-1-piperazinyl]ethyl]cylcohexanol (mixture of cis/trans) | 537 | 1.8 | 35% inhibition | |
| 6 | 1-(2-Pyridinyl)-4-[2-[4-(2-pyridinyl)-1-piperazinyl]ethyl]cyclohexanol (mixture of cis/trans) | 1047 | 0.34 | | |
| 7 | 1-(4-Fluorophenyl)-4-[2-[4-(2-pyridinyl)-1-piperazinyl]ethyl]-cyclohexanol (mixture of cis/trans) | 94% inhibition at 10$^{-5}$ M | 0.64 | 48% inhibition | 16.5 |
| 8 | cis-1-(4-Methoxyphenyl)-4-[2-[4-(2-pyridinyl)-1-piperazinyl]ethyl]-cyclohexanol | 169 | 0.9 | 88% inhibition | |
| 9 | 4-[2-[4-(2-Pyridinyl)-1-piperazinyl]-ethyl]-1-(2-thiazolyl)cyclohexanol (mixture of cis/trans) | 1550 | 1.0 | | |
| 10 | 1-(3-Pyridinyl)-4-[2-[4-(2-pyridinyl)-1-piperazinyl]ethyl]cyclohexanol (mixture of cis/trans) | 847 | 0.37 | | |
| 11 | cis-1-(2-Pyridinyl)-4-[2-[3,6-dihydro-4-phenyl-1(2H)-pyridinyl]ethyl]cyclo-hexanol | 156 | 0.64 | | 3.5 |
| 12 | cis-1-(3-Pyridinyl)-4-[2-[3,6-dihydro-4-phenyl-1(2H)-pyridinyl]ethyl]cyclo-hexanol | 116 | 0.25 | 79% inhibition | |
| 13 | cis-4-[2-(3,6-Dihydro-4-phenyl-1(2H)-pyridinyl)ethyl]-1-(2-thienyl)cyclo-hexanol | 51 | 2 | | |
| 14 | 4-[2-[4-(2-Pyridinyl)-1-piperazinyl]- | 312 | 0.48 | 37% inhibition | 4.5 |

-continued

Biological Activity of Compounds of Formula I

| Example Number | Compound | Inhibiton of [³H]-Spiroperidol Binding IC$_{50}$ nM | Inhibition of Locomotor Activity in Mice ED$_{50}$, mg/kg, IP | Effects on Brain Striatal Dopamine Synthesis in Rats at 10 mg/kg, IP | Inhibition of [³H]DT Binding IC$_{50}$ nM |
|---|---|---|---|---|---|
|  | ethyl]-1-(3-thienyl)cyclohexanol (mixture of cis/trans) |  |  |  |  |
| 15 | trans-1-(4-Methoxyphenyl)-4-[2-[4-(2-pyridinyl)-1-piperazinyl]ethyl]-cyclohexanol | 932 | 0.3 | 52% inhibition |  |
| 16 | trans-4-[[4-(2-Pyridinyl)-1-piperazinyl]-methyl]-1-(2-thienyl)cyclohexanol |  | 4.3 |  |  |
| 17 | cis-4-[[4-(2-Pyridinyl)-1-piperazinyl]-methyl]-1-(2-thienyl)cyclohexanol | 3900 | 5.2 |  |  |
| 18 | trans-1-(2-Pyridinyl)-4-[4-(2-pyrimidinyl)-1-piperazinyl]cyclohexanol |  | >30 |  |  |
| 19 | cis-1-(2-Pyridinyl)-4-[4-(2-pyridinyl)-1-piperazinyl]cyclohexanol |  | 13.0 |  |  |
| 20 | trans-1-(2-Pyridinyl)-4-[4-(2-pyridinyl)-1-piperazinyl]cyclohexanol |  | >30 |  |  |
| 21 | cis-1-(2-Pyridinyl)-4-[4-(2-pyridinyl)-1-piperazinyl]cyclohexanol | 2785 | 2.3 |  |  |
| 22 | trans-1-(3-Pyridinyl)-4-[4-(2-pyridinyl)-1-piperazinyl]cyclohexanol | 12500 | 30 |  |  |
| 23 | cis-1-(3-Pyridinyl)-4-[4-(2-pyridinyl)-1-piperazinyl]cyclohexanol | 1155 | 1.6 |  |  |
| 24 | 4-[4-(2-Pyridinyl)-1-piperazinyl]-1-(2-thienyl)cyclohexanol (mixture of cis/trans) |  | >30 |  |  |
| 25 | 4-[4-(2-Pyridinyl)-1-piperazinyl]-1-(3-thienyl)cyclohexanol (mixture of cis/trans) | 2700 | 2.4 |  |  |
| 26 | 1-(4-Methoxyphenyl)-4-[4-(2-pyridinyl)-1-piperazinyl]cyclohexanol (mixture of cis/trans) | 670 | 0.3 |  |  |
| 27 | 1-Phenyl-4-[4-(2-pyridinyl)-1-piperazinyl]cyclohexanol (mixture of cis/trans) | 1660 | 0.83 |  |  |
| 28 | 4-(3,6-Dihydro-4-phenyl-1(2H)-pyridinyl)-1-(2-pyridinyl)cyclohexanol (mixture of cis/trans) |  | 1.8 |  |  |
| 29 | trans-4-(3,6-Dihyrdo-4-phenyl-1(2H)-pyridinyl)-1-(3-pyridinyl)cyclohexanol |  | 25.6 |  |  |
| 30 | cis-4-(3,6-Dihydro-4-phenyl-1(2H)-pyridinyl)-1-(3-pyridinyl)cyclohexanol | 1250 | 1.3 |  |  |

A compound of Formula Ia

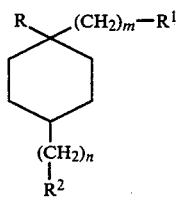

wherein
R is —OH,

wherein R$^4$ is hydrogen, lower alkyl, aryl, aryl lower alkyl, lower alkanoyl, aryl lower alkanoyl, or aroyl,

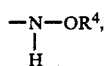

wherein R$^4$ is hydrogen, lower alkyl, aryl, aryl lower alkyl, lower alkanoyl, aryl lower alkanoyl, or aroyl;

m is zero or an integer from 1 to 2;

R$^1$ is aryl, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen;

n is zero or an integer from 1 to 4;

R$^2$ is

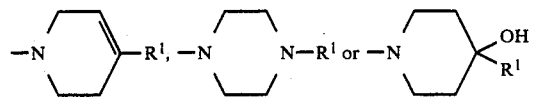

wherein R$^1$ is as defined above; and the corresponding cis and trans isomers thereof; or a pharmaceutically acceptable acid addition salt thereof may be prepared by reacting a compound of Formula II

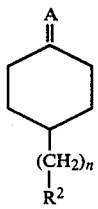

wherein
A is O,
N—R$^4$ wherein R$^4$ is as defined above, or
N—OR$^4$ wherein R$^4$ is as defined above, and
R$^2$ and n are as defined above with a compound of Formula III

    III wherein M is magnesium-Hal, wherein Hal is halogen or M is lithium and R$^1$ and m are as defined above, in the presence of a solvent such as, for example, tetrahydrofuran, diethyl ether, and the like at about −78° C. to about the reflux temperature of the solvent for about 0.5 to about 24 hours to give a compound of Formula Ia.

A compound of Formula Ib

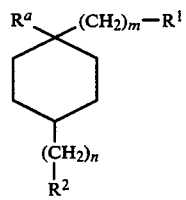

wherein
R$^a$ is —OR$^3$, wherein R$^3$ is lower alkyl, or aryl lower alkyl;
m is zero or an integer from 1 to 2;
R$^1$ is aryl, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen;
n is zero or an integer from 1 to 4;
R$^2$ is

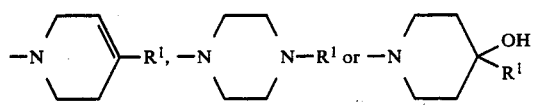

wherein R$^1$ is as defined above; and the corresponding cis and trans isomers thereof; or a pharmaceutically acceptable acid addition salt thereof may be prepared by reacting a compound of Formula Ic

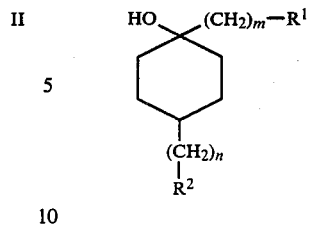

wherein R$^1$, m, n, and R$^2$ are as defined above with a compound of Formula IV R$^3$-Hal    IV wherein Hal is halogen and R$^3$ is as defined above in the presence of a base such as an organic base, for example, triethylamine, pyridine and the like, an inorganic base, for example, an alkali metal or alkaline earth metal hydroxide or carbonate, alkali metal hydride and the like and a solvent such as, for example, dichloromethane, and the like at about −78° C. to about the reflux temperature of the solvent for about 0.5 to about 24 hours to give a compound of Formula Ib.

A compound of Formula Id

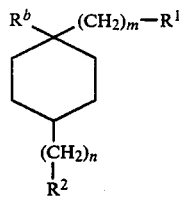

wherein
R$^b$ is —OR$^{3a}$, wherein R$^{3a}$ is lower alkanoyl, aroyl, or aryl lower alkanoyl;
m is zero or an integer from 1 to 2;
R$^1$ is aryl, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen;
n is zero or an integer from 1 to 4;
R$^2$ is

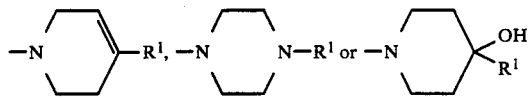

wherein R$^1$ is as defined above; and the corresponding cis and trans isomers thereof; or a pharmaceutically acceptable acid addition salt thereof may be prepared by reacting a compound of Formula Ic with a compound of Formula V

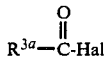    V wherein Hal is halogen and $R^{3a}$ is as defined above using the methodology used to prepare a compound of Formula Ib from a compound of Formula Ic and a compound of Formula IV to give a compound of Formula Id.

A compound of Formula Ie

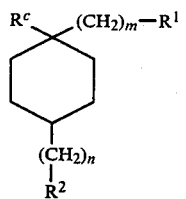 Ie wherein $R^c$ is

wherein $R^4$ and $R^5$ are each independently hydrogen, lower alkyl, aryl, aryl lower alkyl, lower alkanoyl, aryl lower alkanoyl, aroyl, or $R^4$ and $R^5$ are taken together with the nitrogen atom to which they are attached to form a ring denoted by

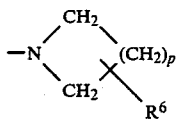

wherein p is zero or an integer from 1 to 4 and $R^6$ is hydrogen or lower alkyl,

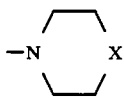

wherein X is oxygen or sulfur or

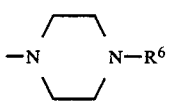

wherein $R^6$ is as defined above, or

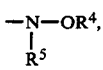

wherein $R^4$ and $R^5$ are each independently hydrogen, lower alkyl, aryl, aryl lower alkyl, lower alkanoyl, aryl lower alkanoyl, aroyl, or $R^4$ and $R^5$ are taken together with the oxygen and nitrogen atoms to which they are attached to form a ring denoted by

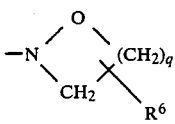

wherein q is an integer from 2 to 3 and $R^6$ is as defined above;

m is zero or an integer from 1 to 2;

$R^1$ is aryl, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen;

n is zero or an integer from 1 to 4;

$R^2$ is

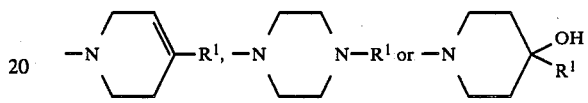

wherein $R^1$ is as defined above; and the corresponding cis and trans isomers thereof; or a pharmaceutically acceptable acid addition salt thereof may be prepared by reacting a compound of Formula VI

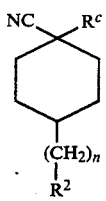 VI wherein $R^c$, $R^2$, and n are as defined above with a compound of Formula III wherein M, $R^1$, and m are as defined above in the presence of a solvent such as, for example, tetrahydrofuran and the like at about 0° C. for about 0.5 to about 24 hours to give a compound of Formula Ie.

A compound of Formula VI is prepared from a compound of Formula IIa

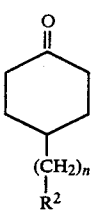 IIa wherein $R^2$ and n are as defined above and a compound of Formula VII R$^c$H  VII wherein $R^c$ is as defined above in the presence of an alkali metal cyanide such as, for example, potassium cyanide and the like and about an equivalent of an acid such as an organic acid, for example, acetic acid and the like, an inorganic acid, for example, hydrochloric acid and the like, in the presence of a solvent such as, for example, methanol, ethanol and the like at about room temperature to give a compound of Formula VI.

A compound of Formula IIa is prepared from a compound of Formula VIII

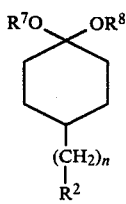 VIII wherein $R^7$ and $R^8$ are alkyl of one to six carbon atoms or $R^7$ and $R^8$ together are

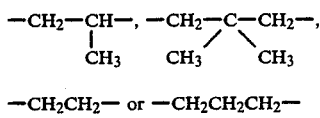

—CH$_2$CH$_2$— or —CH$_2$CH$_2$CH$_2$— and $R^2$ and n are as defined above by treatment with an acid such as, for example, a 10% aqueous solution of hydrochloric acid in the presence of a solvent such as, for example, acetone and the like to give a compound of Formula IIa.

A compound of Formula VIIIa

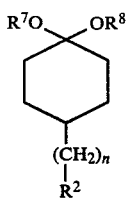 VIIIa wherein n is zero and $R^2$, $R^7$, and $R^8$ are as defined above is prepared from a compound of Formula IX

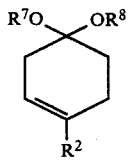 IX wherein $R^2$, $R^7$, and $R^8$ are as defined above by treatment with a reducing agent such as, for example, sodium cyanoborohydride and the like in a solvent such as, for example, methanol and the like in the presence of an acid such as, for example, hydrochloric acid and the like or, alternatively, reduction is carried out with hydrogen in the presence of a catalyst such as, for example, palladium on carbon in the presence of a solvent such as, for example, methanol and the like to give a compound of Formula VIIIa.

A compound of Formula IX is prepared from a compound of Formula X

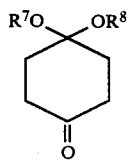 X wherein $R^7$ and $R^8$ are as defined above in the presence of a catalytic amount of an acid such as, for example, para-toluenesulfonic acid and the like in the presence of a solvent suited for the azeotropic removal of water such as, for example, toluene and the like to give a compound of Formula IX.

A compound of Formula VIIIb wherein n is an integer from 1 to 4 and $R^2$, $R^7$, and $R^8$ are as defined above is prepared from a compound of Formula XI

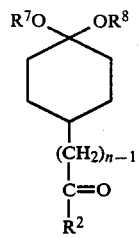 XI wherein n is an integer from 1 to 4 and $R^2$, $R^7$, and $R^8$ are as defined above by treatment with a reducing agent such as, for example, diborane, aluminum hydride and the like in a solvent such as, for example, tetrahydrofuran and the like to give a compound of Formula VIIIb.

A compound of Formula XI is prepared from a compound of Formula XII

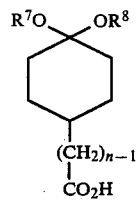 XII wherein n is an integer from 1 to 4 and $R^7$ and $R^8$ are as defined above and a compound of Formula XI. In order to obtain the reaction of these two compounds, a compound of Formula XII must be activated in the presence of a chloroformate such as, for example, isobutyl chloroformate and a base such as, for example, triethylamine, or alternatively, a coupling reagent such as, for example, dicyclohexylcarbodiimide, carbonyldiimidazole and the like in the presence of a solvent such as, for example, dichloromethane and the like to give a compound of Formula XI.

A compound of Formula XII is prepared from a compound of Formula XIII

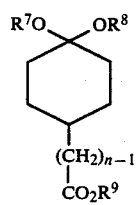 XIII wherein n is an integer from 1 to 4, $R^9$ is lower alkyl and $R^7$ and $R^8$ are as defined above, by hydrolysis with a base such as, for example, potassium hydroxide and the like in an alcohol such as, for example, ethanol and the like to give a compound of Formula XII.

A compound of Formula XIII is prepared from a compound of Formula XIV

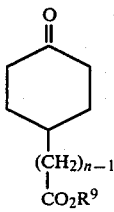

XIV wherein n is an integer from 1 to 4 and $R^9$ is as defined above using conventional procedures known in the art.

Alternatively, a compound of Formula VIIIb is prepared from a compound of Formula XV

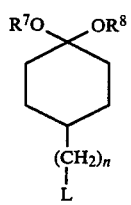

XV wherein n is an integer from 1 to 4, L is halogen, $CH_3SO_2O—$, para-$CH_3C_6H_4SO_2O—$, and the like, and $R^7$ and $R^8$ are as defined above and a compound of Formula XVI $R^2H$    XVI wherein $R^2$ is as defined above in the presence of a base such as, for example, sodium bicarbonate and the like and a solvent such as, for example, dimethylformamide and the like to give a compound of Formula VIIIb.

A compound of Formula XV is prepared from a compound of Formula XVII

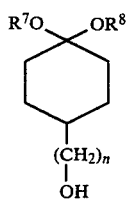

XVII wherein n is an integer from 1 to 4 and $R^7$ and $R^8$ are as defined above by treatment with thionyl chloride, thionyl bromide and the like in the presence of a solvent such as, for example, chloroform and the like or, alternatively, treatment with methanesulfonyl chloride, para-toluenesulfonyl chloride and the like in the presence of a base such as, for example, pyridine and the like to give a compound of Formula XV.

A compound of Formula XVII is prepared from a compound of Formula XIV wherein n is an integer from 1 to 4 and $R^7$, $R^8$, and $R^9$ are as defined above by treatment with a complex metal hydride such as, for example, diborane, lithium aluminum hydride and the like in the presence of a solvent such as, for example, tetrahydrofuran and the like to give a compound of Formula XVII.

A compound of Formula IIb

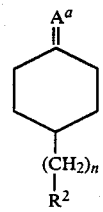

IIb wherein
$A^a$ is N-$R^4$ wherein $R^4$ is as defined above, or
N-$OR^4$ wherein $R^4$ is as defined above and $R^2$ and n are as defined above is prepared from a compound of Formula IIa and a compound of Formula XVIII $R^dH$    XVIII wherein
$R^d$ is

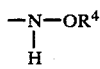

wherein $R^4$ is hydrogen, lower alkyl, aryl, aryl lower alkyl, lower alkanoyl, aryl lower alkanoyl or aroyl,

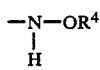

wherein $R^4$ is hydrogen, lower alkyl, aryl, aryl lower alkyl, lower alkanoyl, aryl lower alkanoyl or aroyl in the presence of an acid such as, for example, para-toluenesulfonic acid to give a compound of Formula IIb.

Compounds of Formula III, Formula IV, Formula V, Formula VII, Formula X, Formula XI, Formula XIV, and Formula XVIII are either known or capable of being prepared by methods known in the art. A compound of Formula I may exist as a mixture of cis or trans isomers or as the separate cis or trans isomer. Accordingly, as another aspect of the present invention, a mixture of cis and trans isomers of Formula I may be separated into the individual cis or trans isomer by conventional methodology such as, for example, by fractional crystallization, chromatography and the like.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg preferably 10 mg to 100 mg according to the particular application and the potency of the active component. The composition can, if desired, also contain other compatible therapeutic agents.

In therapeutic use as antipsychotic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired The following nonlimiting examples illustrate the inventors' preferred methods for preparing the compounds of the invention.

EXAMPLE 1 AND EXAMPLE 1a cis- and trans-1-(4-Chlorophenyl)-4-[4-(2-pyridinyl)-1-piperazinyl]cyclohexanol.

A solution of 5.74 g of 1-bromo-4-chlorobenzene in 100 ml anhydrous tetrahydrofuran is cooled to −78° C. under a nitrogen atmosphere. n-Butyllithium (18.75 ml of a 1.6M hexane solution) is added dropwise via syringe. The resulting suspension is stirred at −78° C. for one hour. To this solution is added a solution of 5.19 g of 4-[4-(2-pyridinyl)-1-piperazinyl]cyclohexanone (Example A) in 175 ml of tetrahydrofuran from an addition funnel. The addition of the ketone takes about 15 minutes. The mixture is allowed to warm to room temperature and quenched with 50 ml of saturated ammonium chloride solution. The tetrahydrofuran is evaporated under vacuum and the residue is partitioned into water/dichloromethane. The organic phase is separated, dried over magnesium sulfate, and evaporated in vacuo. The residue is chromatographed on silica gel using 3% methanol:97% dichloromethane as eluant. The less polar isomer in this solvent system is characterized as trans-1-(4-chlorophenyl)-4-[4-(2-pyridinyl)-1-piperazinylcyclohexanol containing 0.15 molecules of chloroform; mp 224°–225° C. (Example 1) and the more polar component is identified as cis-1-(4-chlorophenyl)-4-[4-(2-pyridinyl)-1-piperazinyl]cyclohexanol; mp 183°–185° C. (Example 1a).

In a process analogous to Example 1 and Example 1a using appropriate starting materials the corresponding compounds of Formula I (Examples 2 to 30) are prepared as follows:

EXAMPLE 2

4-[2-4-(2-Pyridinyl)-1-piperazinyl]ethyl]-1-(2-thienyl)cyclohexanol (mixture of cis/trans), containing 0.33 molecules of chloroform; mp 124°–140° C.

EXAMPLE 3 cis-4-[2-[4-(2-Pyridinyl)-1-piperazinyl]ethyl]-1-(2-thienyl)cyclohexanol, hemihydrate; mp 151°–154° C.

EXAMPLE 4 trans-4-[2-[4-(2-Pyridinyl)-1-piperazinyl]ethyl]-1-(2-thienyl)cyclohexanol; mp 108°–109° C.

EXAMPLE 5

1-Phenyl-4-[2-[4-(2-pyridinyl)-1-piperazinyl]ethyl]cyclohexanol (mixture of cis/trans), containing 0.1 molecules of water; mp 158°–163° C.

EXAMPLE 6

1-(2-Pyridinyl)-4-[2-[4-(2-pyridinyl)-1-piperazinyl]ethyl]cyclohexanol (mixture of cis/trans), containing 0.25 molecules of water; mp 100°–105° C.

EXAMPLE 7

1-(4-Fluorophenyl)-4-[2-[4-(2-pyridinyl)-1-piperazinyl]ethyl]cyclohexanol (mixture of cis/trans); mp 172°–177° C.

EXAMPLE 8 cis 1-(4-Methoxyphenyl)-4-[2-[4-(2-pyridinyl)-1-piperazinyl]ethyl]cyclohexanol, containing 0.2 molecules of water; mp 142°–144° C.

EXAMPLE 9

4-[2-4-(2-Pyridinyl)-1-piperazinyl]ethyl]-1-(2-thiazolyl)cyclohexanol (mixture of cis/trans), containing 0.75 molecules of chloroform; mp 65°–80° C.

EXAMPLE 10

1-(3-Pyridinyl)-4-2-4-(2-pyridinyl)-1-piperazinyl]ethyl]cyclohexanol (mixture of cis/trans), containing 0.2 molecules of water; mp 128°–148° C.

EXAMPLE 11 cis-1-(2-Pyridinyl]-4-[2-[3,6-dihydro-4-phenyl-1H(2H)-pyridinyl]ethyl]cyclohexanol; mp 153°–156° C.

EXAMPLE 12 cis-1-(3-Pyridinyl)-4-[2-[3,6-dihydro-4-phenyl-1(2H)-pyridinyl]ethyl]cyclohexanol; mp 160°–163° C.

EXAMPLE 13 cis-4-[2-(3,6-Dihydro-4-phenyl-1(2H)-pyridinyl)ethyl]-1-(2-thienyl)cyclohexanol, containing 0.1 molecules of water; mp 164°–170° C.

EXAMPLE 14

4-[2-[4-(2-Pyridinyl)-1-piperazinyl]ethyl]-1-(3-thienyl)cyclohexanol (mixture of cis/trans), containing 0.2 molecules of water; mp 115°–129° C.

EXAMPLE 15 trans-1-(4-Methoxyphenyl)-4-[2-[4-(2-pyridinyl)-1-piperazinyl]ethyl]cyclohexanol, containing 0.2 molecules of water; mp 127°–131° C.

EXAMPLE 16 trans-4-[[4-(2-Pyridinyl)-1-piperazinyl]methyl]-1-(2-thienyl)cyclohexanol; mp 50°–52° C.

EXAMPLE 17 cis -4-[[4-(2-Pyridinyl)-1-piperazinyl]methyl]-1-2-thienyl)cyclohexanol, trihydrochloride, containing 2.5 molecules of water; mp 114°–117° C.

EXAMPLE 18 trans-1-(2-Pyridinyl)-4-[4-(2-pyrimidinyl)-1-piperazinyl]cyclohexanol; mp 240°–242° C.

EXAMPLE 19 cis-1-(2-Pyridinyl)-4-[4-(2-pyrimidinyl)-1-piperazinyl]cyclohexanol, trihydrochloride, containing 3.5 molecules of water; mp 138°–140° C.

EXAMPLE 20 trans-1-(2-Pyridinyl)-4-[4-(2-pyridinyl)-1-piperazinyl]cyclohexanol, containing 0.25 molecules of water; mp 86°–93° C.

EXAMPLE 21 cis-1-(2-Pyridinyl)-4-[4-(2-pyridinyl)-1-piperazinyl]cyclohexanol, containing 0.4 molecules of water; mp 130°–134° C.

EXAMPLE 22 trans-1-(3-Pyridinyl)-4-[4-(2-pyridinyl)-1-piperazinyl]cyclohexanol; mp 153°–158° C.

EXAMPLE 23 cis -1-(3-Pyridinyl)-4-[4-(2-pyridinyl)-1-piperazinyl]cyclohexanol, hemihydrate; mp 175°–179° C.

EXAMPLE 24

4-[4-(2-Pyridinyl)-1-piperazinyl]-1-(2-thienyl)cyclohexanol (mixture of cis/trans); mp 130°–135° C.

EXAMPLE 25

4-[4-(2-Pyridinyl)-1-piperazinyl]-1-(3-thienyl)cyclohexanol (mixture of cis/trans); mp 140°–155° C.

EXAMPLE 26

1-(4-Methoxyphenyl)-4-[4-(2-pyridinyl)-1-piperazinyl]cyclohexanol (mixture of cis/trans); mp 154°–157° C.

EXAMPLE 27

1-Phenyl-4-[4-(2-pyridinyl)-1-piperazinyl]cyclohexanol (mixture of cis/trans), containing 0.25 molecules of water; mp 164°–172° C.

EXAMPLE 28

4-(3,6-Dihydro-4-phenyl-1(2H)-pyridinyl)-1-(2-pyridinyl)cyclohexanol (mixture of cis/trans); mp 157°–159° C.

EXAMPLE 29 trans-4-(3,6-Dihydro-4-phenyl-1(2H)-pyridinyl)-1-(3-pyridinyl)cyclohexanol; mp 124°–125° C.

EXAMPLE 30 cis-4-[3,6-Dihydro-4-phenyl-1(2H)-pyridinyl]-1-(3-pyridinyl)cyclohexanol; mp 199°–200° C.

PREPARATION OF STARTING MATERIALS

EXAMPLE A

4-[4-(2-Pyridinyl)-1-piperazinyl]cyclohexanone.

A solution of 1,4-cyclohexanedione monoethyleneketa (50.0 g), 1-(2-pyridyl)piperazine (52.16 g), and p-toluenesulfonic acid (0.5 g) in 500 ml of toluene is refluxed with a Dean-Stark trap until the theoretical amount of water is collected (about four hours). The solvent is evaporated in vacuo and the residue is dissolved in 750 ml of methanol. This solution is cooled in an ice bath and sodium cyanoborohydride (30.1 g) is added in small portions over a two-minute period. The resulting suspension is stirred mechanically and over the next 30 minutes enough concentrated hydrochloric acid solution is added dropwise to the reaction mixture to maintain a pH of about 4. The solvent is removed in vacuo to leave a semisolid residue which is dissolved in 300 ml of a 10% solution of hydrochloric acid in a well ventilated fume hood. This solution is diluted with an equal volume of acetone and refluxed for two hours. The volatile components of the mixture are removed in vacuo and the residue is cooled in an ice bath and made basic with concentrated ammonium hydroxide. The white solid which forms is recrystallized from ethyl acetate-heptane to give 52.4 g of the title compound; mp 142°–144° C.

We claim:

1. A compound of Formula I

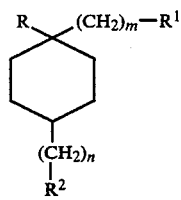

wherein

R is —OR$^3$, wherein R$^3$ is hydrogen, lower alkyl, phenyl lower alkyl, phenyl lower alkyl substituted by one to four substituents selected from the group consisting of lower alkyl, lower alkoxy, lower thioalkoxy, halogen and trifluoromethyl, lower alkanoyl, phenylcarbonyl, phenylcarbonyl substituted by one to four substituents selected from the group consisting of lower alkyl, lower alkoxy, lower thioalkoxy, halogen and trifluoromethyl, or phenyl lower alkanoyl, phenyl lower alkanoyl substituted by one to four substituents selected from the group consisting of lower alkyl, lower alkoxy, lower thioalkoxy, halogen and trifluoromethyl,

wherein R$^4$ and R$^5$ are each independently hydrogen, lower alkyl, phenyl, phenyl substituted by one to four substituents selected from the group consisting of lower alkyl, lower alkoxy, lower thioalkoxy, halogen and trifluoromethyl, phenyl lower alkyl, phenyl lower alkyl substituted by one to four substituents selected from the group consisting of lower alkyl, lower alkoxy, lower thioalkoxy, halogen and trifluoromethyl, lower alkanoyl, phenyl lower alkanoyl, phenyl lower alkanoyl substituted by one to four substituents selected from the group consisting of lower alkyl, lower alkoxy, lower thioalkoxy, halogen and trifluoromethyl, phenylcarbonyl, phenylcarbonyl substituted by one to four substituents selected from the group consisting of lower alkyl, lower alkoxy, lower thioalkoxy, halogen and trifluoromethyl, or R$^4$ and R$^5$ are taken together with the nitrogen atom to which they are attached to form a ring denoted by

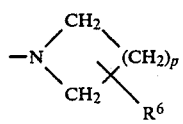

wherein p is zero or an integer from 1 to 4 and R$^6$ is hydrogen or lower alkyl,

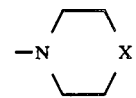

wherein X is oxygen or sulfur or

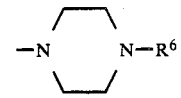

wherein R$^6$ is as defined above, or

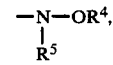

wherein R$^4$ and R$^5$ are each independently hydrogen, lower alkyl, phenyl, phenyl substituted by one to four substituents selected from the group consisting of lower alkyl, lower alkoxy, lower thioalkoxy, halogen and trifluoromethyl, phenyl lower alkyl, phenyl lower alkyl substituted by one to four substituents selected from the group consisting of lower alkyl, lower alkoxy, lower thioalkoxy, halogen and trifluoromethyl, lower alkanoyl, phenyl lower alkanoyl, phenyl lower alkanoyl substituted by one to four substituents selected from the group consisting of lower alkyl, lower alkoxy, lower thioalkoxy, halogen and trifluoromethyl, phenylcarbonyl, phenylcarbonyl substituted by one to four substituents selected from the group consisting of lower alkyl, lower alkoxy, lower thioalkoxy, halogen and trifluoromethyl, or R$^4$ and R$^5$ are taken together with the oxygen and nitrogen atoms to which they are attached to form a ring denoted by

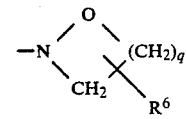

wherein q is an integer from 2 to 3 and R$^6$ is as defined above;

m is zero or an integer from 1 to 2;

R$^1$ is phenyl, phenyl substituted by one to four substituents selected from the group consisting of lower alkyl, lower alkoxy, lower thioalkoxy, halogen and trifluoromethyl, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or substituted by lower alkyl or halogen;

n is zero or an integer from 1 to 4;

R$^2$ is

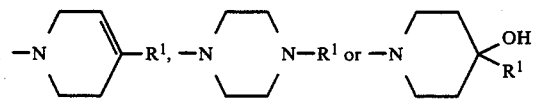

wherein R¹ is as defined above; and the corresponding cis and trans isomers thereof; or a pharmaceutically acceptable acid addition salt thereof.

2. A compound according to claim 1, in which
R is —OR³, wherein R³ is hydrogen or lower alkanoyl,

wherein R⁴ is hydrogen or lower alkanoyl and R⁵ is hydrogen or

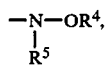

wherein one of R⁴ or R⁵ is hydrogen and the other is hydrogen, lower alkyl, phenyl, phenyl substituted by one to four substituents selected from the group consisting of lower alkyl, lower alkoxy, lower thioalkoxy, halogen and trifluoromethyl, or lower alkanoyl;
m is zero;
R¹ is phenyl, phenyl substituted by para lower alkyl, para lower alkoxy, para lower thioalkoxy, or para halogen, 2-, 3-, or 4-pyridinyl, 2- or 3-furanyl, 2- or 3-thienyl, 2-, 4-, or 5-thiazolyl, or 2-, 4-, or 5-pyrimidinyl;
n is zero or an integer from 1 to 3; and
R² is

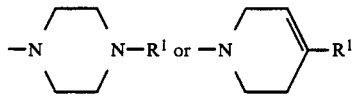

wherein R¹ is as defined above.

3. A compound according to claim 2, in which
R is —OH, —NH², or —NHOR⁴, wherein R⁴ is hydrogen, lower alkyl, phenyl, phenyl substituted by one to four substituents selected from the group consisting of lower alkyl, lower alkoxy, lower thioalkoxy, halogen and trifluoromethyl, or lower alkanoyl;
m is zero;
R¹ is phenyl, phenyl substituted para lower alkoxy or para halogen, 2-, 3-, or 4-pyridinyl, 2- or 3-thienyl, 2-, 4-, or 5-thiazolyl, or 2-, 4-, or 5-pyrimidinyl;
n is zero or an integer from 1 to 2; and
R² is

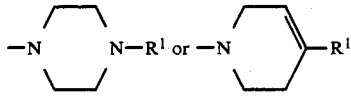

wherein R¹ is as defined above.

4. A compound according to claim 3 selected from the group consisting of
4-[2-[4-(2-Pyridinyl)-1-piperazinyl]ethyl]-1-(2-thienyl)-cyclohexanol (mixture of cis/trans);
cis-4-[2-[4-(2-Pyridinyl)-1-piperazinyl]ethyl]-1-(2-thienyl) cyclohexanol;
trans-4-[2-[4-(2-Pyridinyl)-1-piperazinyl]ethyl]-1-(2-thienyl) cyclohexanol;
1-Phenyl-4-[2-[4-(2-pyridinyl)-1-piperazinyl]-ethyl]cyclohexanol (mixture of cis/trans);
1-(2-Pyridinyl)-4-[2-[4-(2-pyridinyl)-1-piperazinyl]ethyl]cyclohexanol (mixture of cis/trans);
1-(4-Fluorophenyl)-4-[2-[4-(2-pyridinyl)-1-piperazinyl]ethyl]cyclohexanol (mixture of cis/trans);
cis-1-(4-Methoxyphenyl)-4-[2-[4-(2-pyridinyl)-1-piperazinylethyl]cyclohexanol;
trans-1-(4-Methoxyphenyl)-4-[2-[4-(2-pyridinyl)-1-piperazinyl]ethyl]cyclohexanol;
4-[2-[4-(2-Pyridinyl)-1-piperazinyl]ethyl]-1-(2-thiazolyl)cyclohexanol (mixture of cis/trans);
1-(3-Pyridinyl)-4-[2-[4-(2-pyridinyl)-1-piperazinyl]ethyl]cyclohexanol (mixture of cis/trans);
cis-1-(2-Pyridinyl)-4-[2-[3,6-dihydro-4-phenyl-1(2H)-pyridinyl]-ethylcyclohexanol;
cis-1-(3-Pyridinyl)-4-[2-[3,6-dihydro-4-phenyl-1(2H)-pyridinyl]ethyl]cyclohexanol;
cis-4-[2-(3,6-Dihydro-4-phenyl-1(2H)-pyridinyl)ethyl]-1-(2-thienyl)cyclohexanol;
4-[2-[4-(2-Pyridinyl)-1-piperazinyl]ethyl]-1-(3-thienyl)-cyclohexanol (mixture of cis/trans);
trans-4-[[4-(2-Pyridinyl)-1-piperazinyl]methyl]-1-(2-thienyl)cyclohexanol;
cis-4-[[4-(2-Pyridinyl)-1-piperazinyl]methyl]-1-(2-thienyl)cyclohexanol;
trans-1-(2-Pyridinyl)-4-[4-(2-pyrimidinyl)-1-piperazinyl]cyclohexanol;
cis-1-(2-Pyridinyl)-4-[4-(2-pyrimidinyl)-1-piperazinyl]cyclohexanol;
trans-1-(2-Pyridinyl)-4-[4-(2-pyridinyl)-1-piperazinyl]cyclohexanol;
cis-1-(2-Pyridinyl)-4-[4-(2-pyridinyl)-1-piperazinylcyclohexanol;
trans-1-(3-Pyridinyl)-4-[4-(2-pyridinyl)-1-piperazinyl]cyclohexanol;
cis-1-(3-Pyridinyl)-4-[4-(2-pyridinyl)-1-piperazinyl]cyclohexanol;
4-[4-(2-Pyridinyl)-1-piperazinyl]-1-(2-thienyl)cyclohexanol (mixture of cis/trans);
4-[4-(2-Pyridinyl)1-piperazinyl]-1-(3-thienyl)cyclohexanol (mixture of cis/trans); .
trans-1-(4-Chlorophenyl)-4-[4-(2-pyridinyl)-1-piperazinyl]cyclohexanol;
cis-1-(4-Chlorophenyl)-4-[4-(2-pyridinyl)-1-piperazinyl]cyclohexanol;
1-(4-Methoxyphenyl)-4-[4-(2-pyridinyl)-1-piperazinyl]cyclohexanol (mixture of cis/trans);
1-Phenyl-4-[4-(2-pyridinyl)-1-piperazinyl]cyclohexanol (mixture of cis/trans);
4-(3,6-Dihydro-4-phenyl-1(2H)-pyridinyl)-1-(2-pyridinyl)cyclohexanol (mixture of cis/trans);
trans-4-(3,6-Dihydro-4-phenyl-1(2H)-pyridinyl)-1-(3-pyridinyl)cyclohexanol; and
cis-4-[3,6-Dihydro-4-phenyl-1(2H)-pyridinyl]-1-(3-pyridinyl)cyclohexanol.

5. A method of treating schizophrenia comprising administering to a host suffering therefrom a therapeutic effective amount of a compound according to claim 1 in unit dosage form.

6. A pharmaceutical composition adapted for administration as a dopaminergic, antipsychotic, antihypertensive or antidepressant agent comprising a therapeutic effective amount of a compound according to claim 1 in admixture with a pharmaceutically acceptable excipient, diluent or carrier.

* * * * *

UNITED STATES PATENT AND TRADEMARK OFFICE
CERTIFICATE OF CORRECTION

PATENT NO. : 4,957,921

DATED : September 18, 1990

INVENTOR(S) : Bradley W. Caprathe, et al

It is certified that error appears in the above—identified patent and that said Letters Patent is hereby corrected as shown below:

```
In column 24, line 65-66,
delete "or substituted by lower alkyl" and
insert at line 66 after halogen --, 2-, 4-
or 5-thiazolyl or 2-, 4- or 5-thiazolyl
substituted by lower alkyl or halogen--

In column 26, line 11
delete "piperazinylethyl" and
insert --piperazinyl]ethyl--

In column 26, line 35,
delete "piperazinylcy-" and
insert --piperazinyl]cy--
```

Signed and Sealed this

Seventeenth Day of March, 1992

*Attest:*

HARRY F. MANBECK, JR.

*Attesting Officer*     *Commissioner of Patents and Trademarks*